US005536084A

United States Patent [19]
Curtis et al.

[11] Patent Number: 5,536,084
[45] Date of Patent: Jul. 16, 1996

[54] MOBILE NURSING UNIT AND SYSTEM THEREFOR

[75] Inventors: Grace E. Curtis, Waynesville; Cynthia S. Livezey, Fairborn; Gary D. McDonnell, Huber Heights; Mark L. Grady, Brookville; Richard J. Minor, Spring Valley, all of Ohio

[73] Assignee: Grandview Hospital and Medical Center, Dayton, Ohio

[21] Appl. No.: 240,162

[22] Filed: May 9, 1994

[51] Int. Cl.$^6$ ................................................. G06F 15/00
[52] U.S. Cl. .................................................. 364/413.01
[58] Field of Search ........................................ 364/413.01

[56] References Cited

U.S. PATENT DOCUMENTS

| | | |
|---|---|---|
| 4,489,387 | 12/1984 | Lamb et al. . |
| 4,857,713 | 8/1989 | Brown . |
| 4,897,662 | 1/1990 | Lee et al. . |
| 4,955,038 | 9/1990 | Lee et al. . |
| 4,967,108 | 10/1990 | Lee et al. . |
| 4,967,928 | 11/1990 | Carter . |
| 4,984,291 | 1/1991 | Dias et al. . |
| 5,008,821 | 4/1991 | Pratt et al. . |
| 5,025,486 | 6/1991 | Klughart . |
| 5,057,677 | 10/1991 | Bertagna et al. . |
| 5,072,383 | 12/1991 | Brimm et al. . |
| 5,077,666 | 12/1991 | Brimm et al. . |

OTHER PUBLICATIONS

Brochure entitled "New Visions–Leadership in Intergrated Clinical Information Systems" from CliniCom®, pp.1–10.
Brochure entitled "Vitalnet™ System–Decision 2000–a Nursing Information Network" from Critikon, Inc., 1993.
Brochure entitled "Introducing the Care Station™ 1000 Mobile Bedside Unit" from Critikon, Inc., 1992.

*Primary Examiner*—William E. Kamm
*Attorney, Agent, or Firm*—Killworth, Gottman, Hagan & Schaeff

[57] ABSTRACT

A mobile nursing unit comprises a cart which stores and transports medications and medical supplies and a computer system mounted on the cart for transmitting and receiving data as a nurse performs patient rounds. The cart includes a medication storage compartment which may be locked for storing medications. The computer system comprises a central processing unit and a transmitter and receiver device responsive to the central processing unit for transmitting and receiving data in real-time during rounds. Preferably, the transmitter and receiver device transmits and receives data through spread spectrum radio frequency signals. A system for providing patient care and for documenting patient care is also provided which includes a remote computer and a plurality of mobile nursing units as described above. A printer is connected to the remote computer to print patient forms. A nurse is thus able to update patient forms immediately before or after performing a task, such as dispensing medication, and print the updated patient forms while continuing with the patient round.

20 Claims, 10 Drawing Sheets

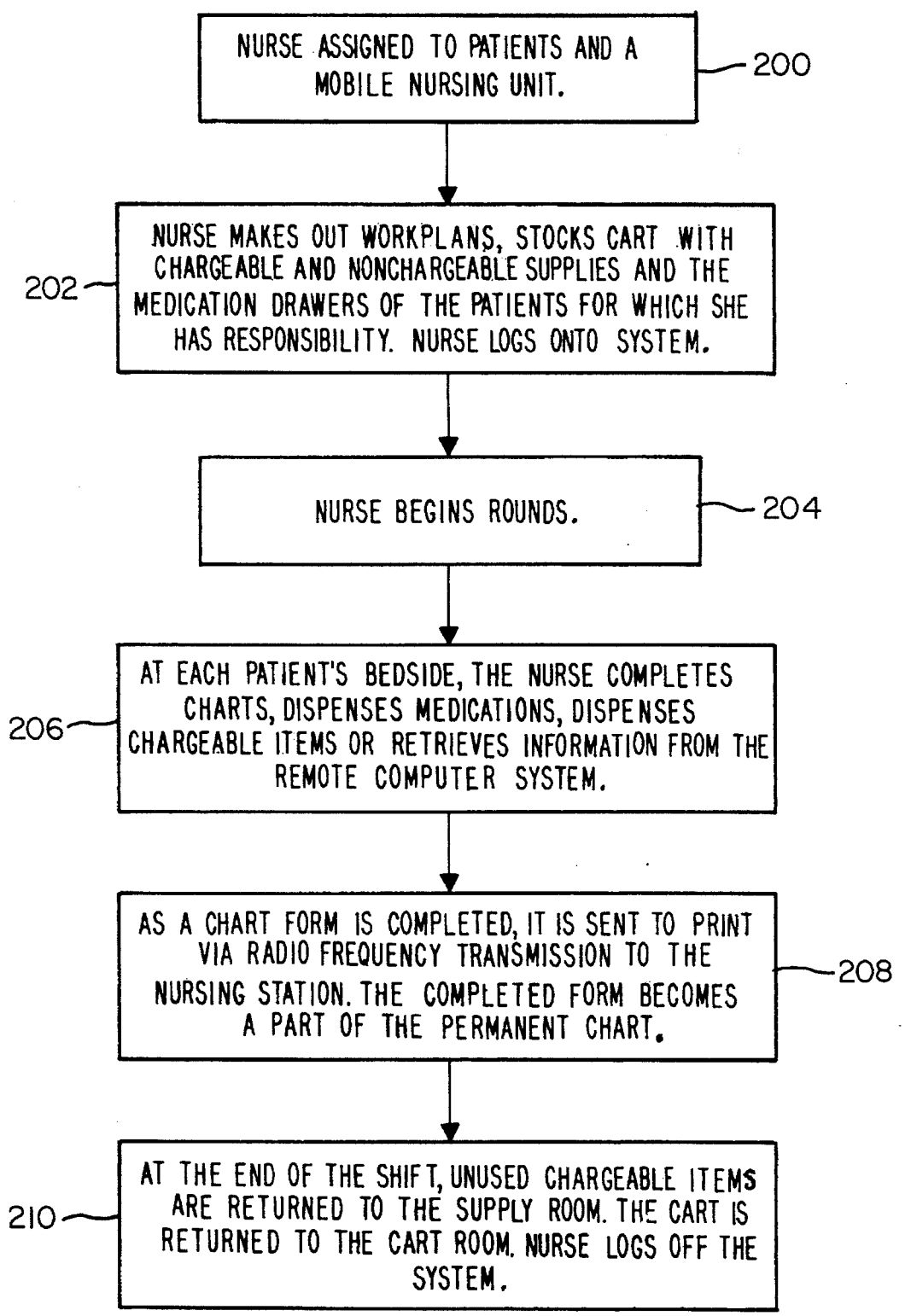

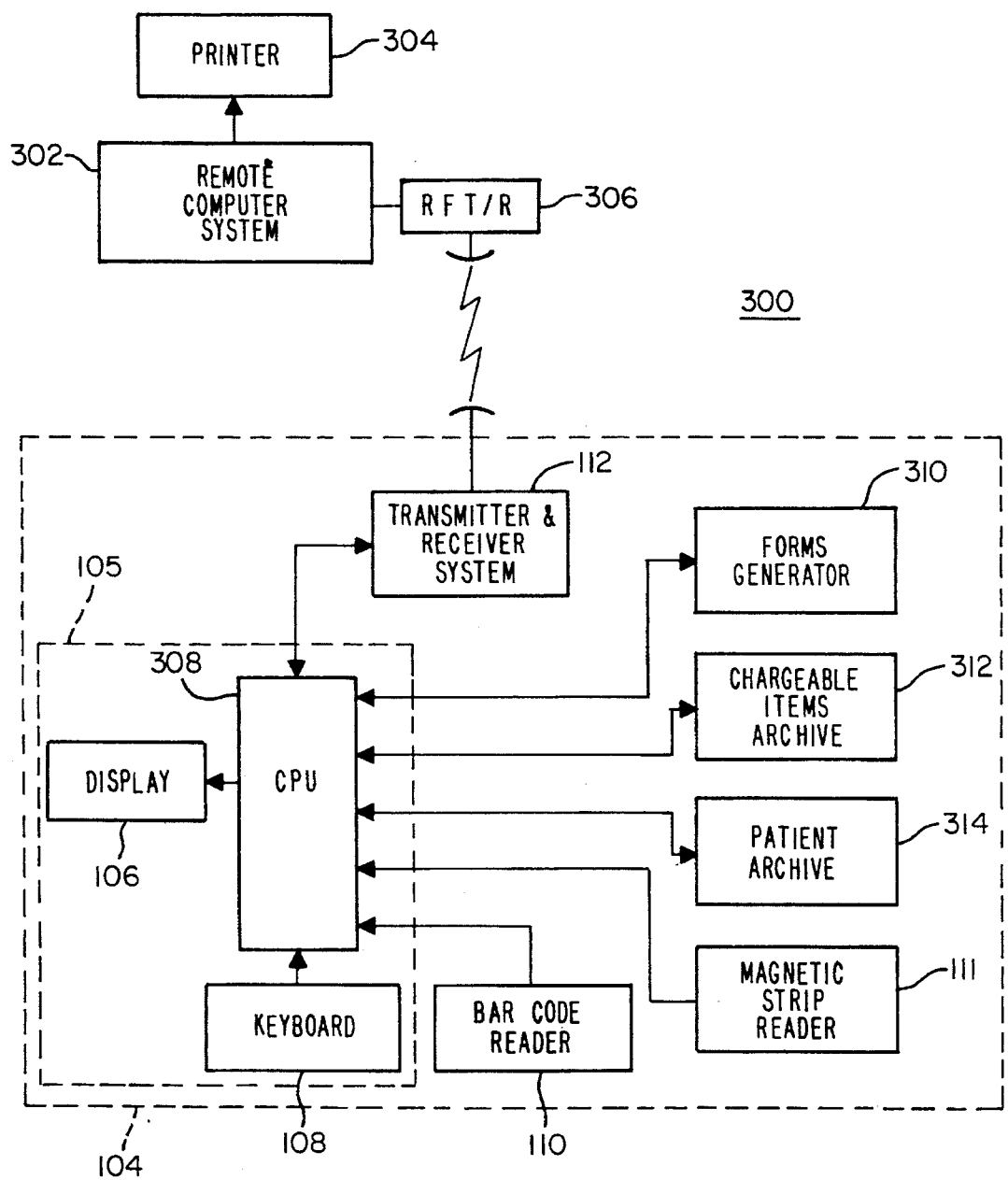

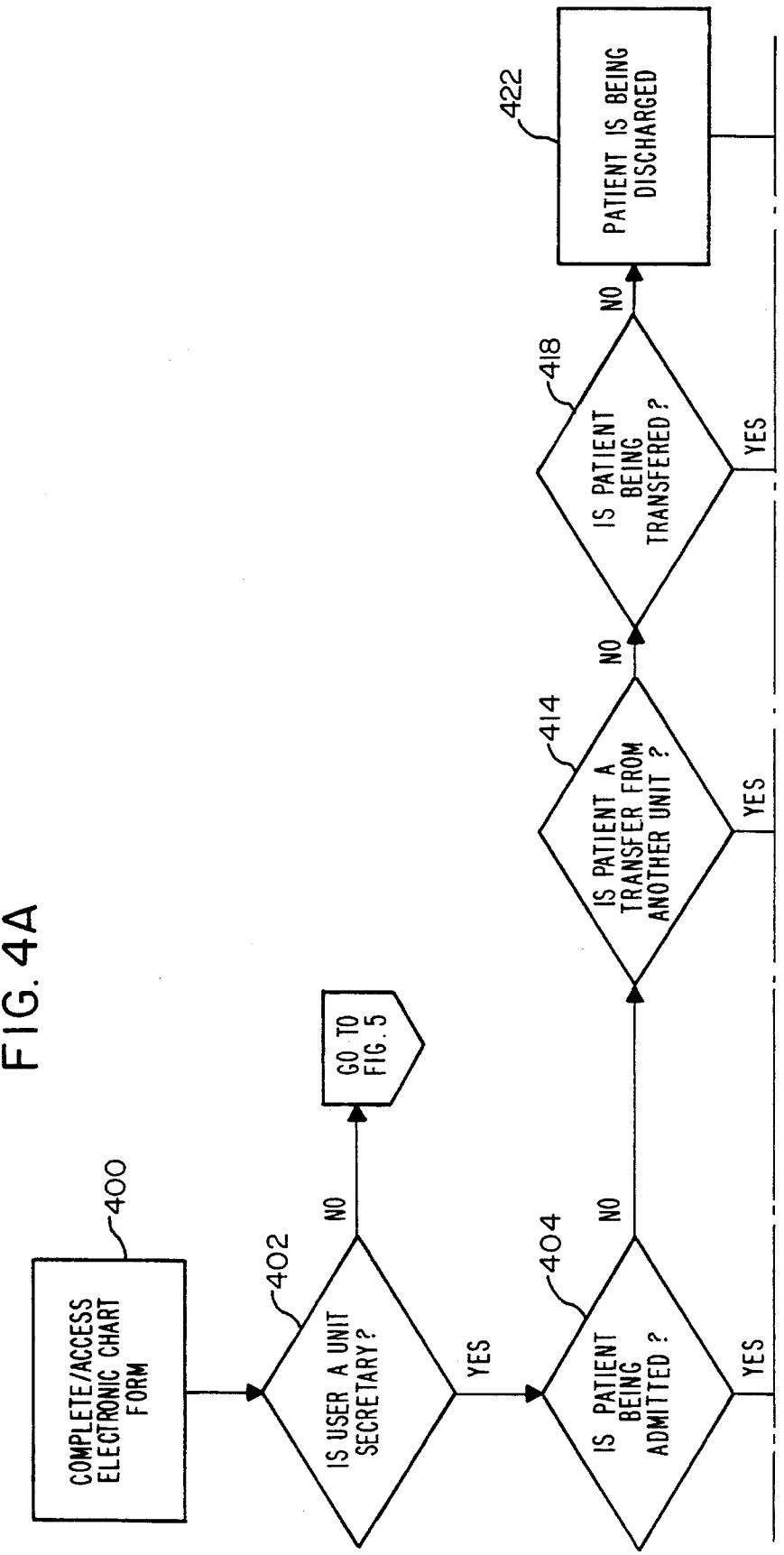

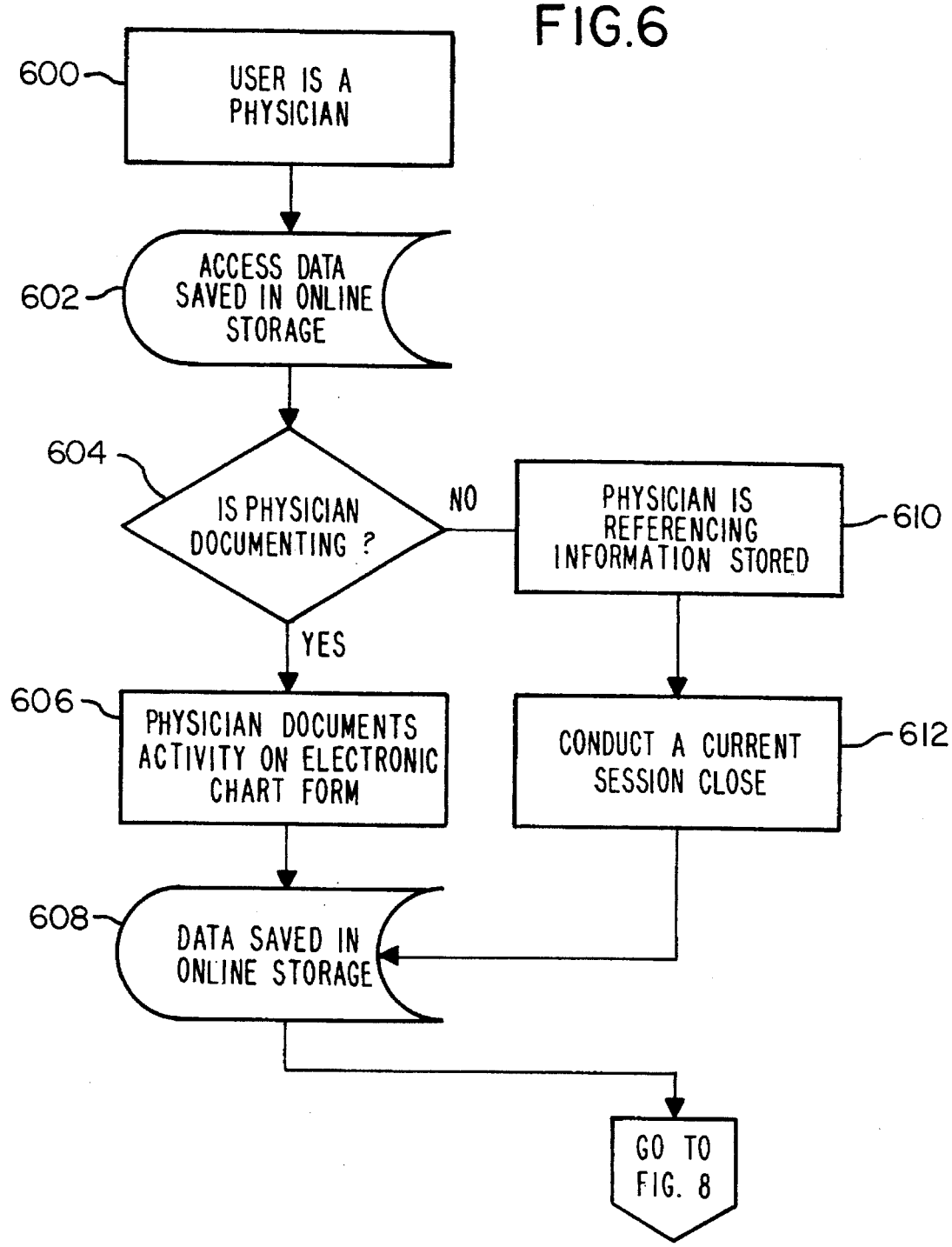

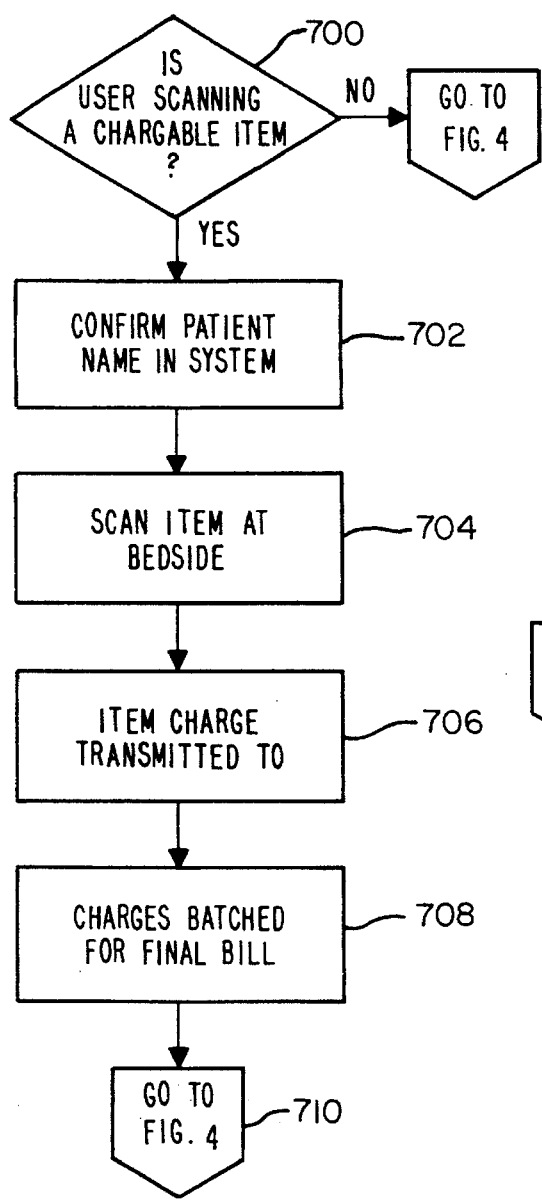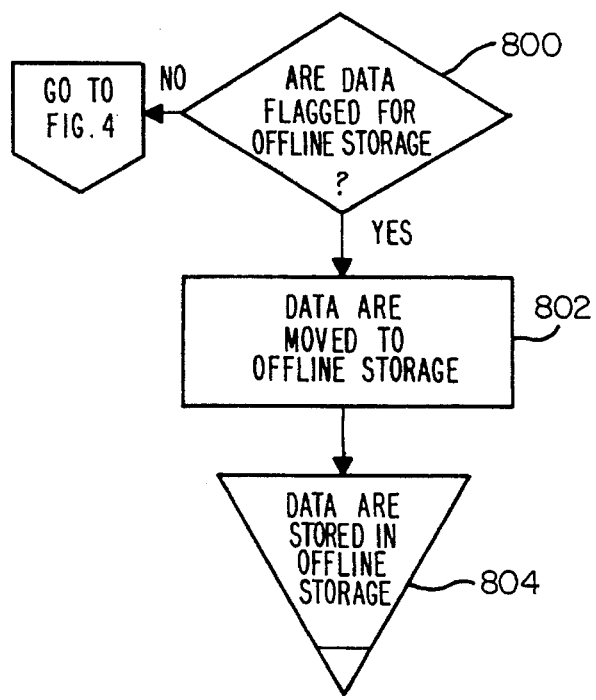

MOBILE NURSING UNIT AND SYSTEM THEREFOR

BACKGROUND OF THE INVENTION

The present invention relates generally to mobile nursing carts and, more particularly, to a mobile nursing unit including a cart for storing and transporting medications and other medical supplies and a computer system mounted on the cart for storing patient information, for recording patient information and for retrieving patient information from a remote computer via spread spectrum radio frequency signals.

Typically, a nurse is responsible for several patients located at or near a centralized nursing station. At the beginning of a shift, the nursing personnel perform medication rounds during which the appropriate medications are administered to the various patients. A nurse initially loads a medication cart with the medications needed for a medication round. The nurse determines the quantities and types of medications needed by examining the individual orders from the treating physicians for each of her assigned patients.

During a round, the nurse must also review the patient's chart, which is typically mounted on the bed of the patient, to ensure the correct administration of medication. Each administration of medication must then be properly recorded and verified on a multitude of charts and forms.

Other medical supplies, such as bandages, gauze, intravenous tubing, needles, etc., may also be dispensed during the nurse's round. Oftentimes, a nurse must retrieve required medical supplies from a centralized supply closet. This procedure is time consuming and tedious.

In addition, each of the medical supplies are typically charged to the patient on an "as used" basis and, consequently, an accurate record of the medical supplies expended on a particular patient is required for billing purposes. The nurse thus needs to complete additional forms relating to the use of medical supplies.

All of these procedures are very tedious and time consuming. The attention given to a patient is thus necessarily reduced due to the nurse spending a significant amount of time doing clerical work and retrieving supplies from the supply closet. Human recorders are also prone to provide inaccurate or incomplete information. These problems are exacerbated when the human recorder has to put forth a great deal of effort in the recording process. Further time is consumed detecting and resolving errors in the record.

Medication carts are known in the art. For example, U.S. Pat. No. 4,967,928, issued to Carter, discloses a medication cart including a locked compartment for storing and dispensing narcotics and another compartment for non-narcotic medications. The cart also includes all onboard computer system having an input device, such as a bar reader, card reader or keyboard. At the beginning of a round, information regarding individual patients, such as medication orders, and the supplies on the cart, such as narcotics inventory, is transferred into a memory in the computer system. This information may be transferred into the memory by use of one or more input devices or downloaded from a remote computer.

During a round, the amount and type of medications dispensed are recorded by the computer system. At the end of the round, the computer system is connected to a printer via a conventional plug and socket and the record for each patient is printed and placed in the patient's chart.

Unfortunately, the Carter cart does not provide for real-time transfer and retrieval of information as the nurse makes a round. Periodically, unforeseen circumstances arise wherein the nurse requires additional information. Additionally, the Carter cart must be hardwired to a printer and, consequently, either a printer must be transported with each cart, which is cumbersome and relatively expensive, or the cart must be connected to a remote printer after the round. Accordingly, there is a need in the art for a mobile nursing unit for transporting medications and medical supplies which transmits and records information through radio frequency signals, which provides for updating and printing of records at a remote printer and which provides for a record of chargeable medical supplies expended.

SUMMARY OF THE INVENTION

A mobile nursing unit facilitates the transportation and dispersion of medications and other medical supplies and provides real-time data access as a nurse performs patient rounds. The nursing unit includes a cart for storing and transporting medications and medical supplies and a computer system for providing real-time data access and data input by the nurse. A transmitter and receiver device in the computer system transmits and receives data through radio frequency signals, thus permitting real time transfer of data with a remote computer as the nursing unit is being moved throughout a health care facility, such as a hospital.

In accordance with one aspect of the present invention, a mobile nursing unit comprises a cart for storing and transporting medicines and medical supplies. The cart includes a plurality of wheels mounted thereon for permitting movement of the cart. A computer system is mounted on the cart for transmitting and receiving data. The computer system includes a central processing unit and a transmitter and receiver device responsive to the central processing unit for transmitting and receiving data. The transmitter and receiver system is capable of transmitting and receiving data through radio frequency signals. An input device, such as a keyboard, bar code reader, magnetic strip reader or the like, is provided for inputting data into the computer system. Data is displayed on a display responsive to the central processing unit.

The cart may include a waste compartment for disposing of waste. A medication storage compartment in the cart stores medications as the nurse makes patient rounds. For security reasons, the cart may comprise a lock for locking medications in the medication storage compartment.

To facilitate the nurse's duties, the computer system comprises a forms generator responsive to the central processing unit for generating a plurality of forms for charting patient care. The computer system may comprise a patient archive responsive to the central processing unit for storing information concerning patients. The central processing unit may comprise a chargeable item archive for identifying and storing medical supplies used on a patient to facilitate preparing the patient's medical bill.

Since many nursing units may be operating at a single health care facility, the transmitter and receiver device may comprise a spread spectrum transmitter and receiver for transmitting and receiving data.

In accordance with another aspect of the present invention, a mobile nursing unit comprises a cart including a medication storage compartment for storing medications, a medical supplies compartment for storing medical supplies, and a waste compartment for storing waste. The medication storage compartment includes a lock for locking the medication storage compartment. A plurality of wheels permit free movement of the cart. A computer system is mounted on the cart and includes a central processing unit and a transmitter and receiver system responsive to the central processing unit for transmitting and receiving data. The transmitter and receiver system is capable of transmitting and receiving data through radio frequency signals and of operating over a spread spectrum. A display is provided responsive to the central processing unit for displaying data. An input device is provided for inputting data into the computer system. The computer system may comprise a chargeable item archive responsive to the central processing unit for identifying and recording the type and amount of medical supplies used for each patient.

In accordance with yet another aspect of the present invention, a system for providing patient care and for documenting patient care is provided. The system comprises a remote computer system for transmitting data, for storing data and for receiving data. The remote computer system includes a remote transmitter and receiver device for transmitting and receiving data through radio frequency signals. A printer responsive to the remote computer system prints documents indicative of patient care. A plurality of mobile nursing units are provided. Each of the units comprises a cart for storing medications and medical supplies, the cart including a plurality of wheels for permitting movement of the cart, and a computer system mounted on the cart. The computer system comprises a central processing unit, a unit transmitter and receiver device for transmitting data to the remote transmitter and receiver device and for receiving data from the remote transmitter and receiver device, the unit transmitter and receiver device being capable of transmitting and receiving data through radio frequency signals, an input device, such as a bar code reader, for inputting data into the computer system, and a display responsive to the central processing unit for displaying data.

The cart may comprise a medication storage compartment for storing medications; and a lock for locking medications in the medication storage compartment. The computer system may comprise a forms generator responsive to the central processing unit for generating a plurality of forms for charting patient care. Preferably, the unit transmitter and receiver device transmits and receives the radio frequency signals in spread spectrum format and the remote transmitter and receiver device transmits and receives the radio frequency signals in spread spectrum format.

These and other features and advantages of the present invention will become apparent from the following detailed description, the accompanying drawings and the appended claims.

BRIEF DESCRIPTION OF THE DRAWINGS

FIG. 2 is a flow chart illustrating an exemplary operational sequence of a nurse employing the mobile nursing unit shown in FIG. 1;

FIG. 3 is a schematic diagram of a system for providing patient care and for documenting patient care including a mobile computer system and a remote computer system in accordance with the present invention; and FIGS. 4 through 8 are flow charts illustrating the operation of the mobile nursing unit and system schematically shown in FIG. 3.

DETAILED DESCRIPTION OF THE INVENTION

Figure 1:
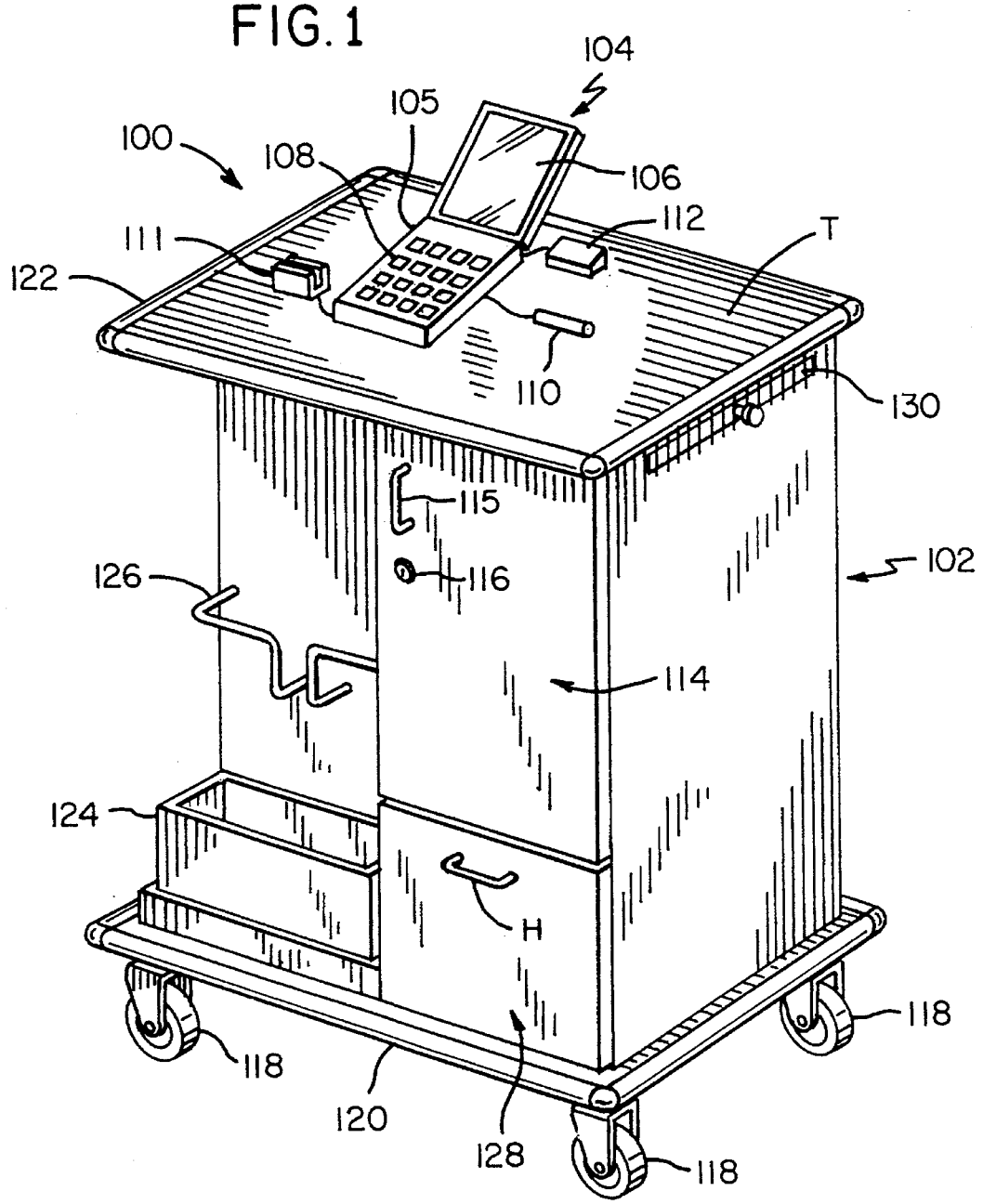
FIG. 1 is a perspective view of a mobile nursing unit in accordance with the present invention.

A mobile nursing unit 100 including a cart 102 and a computer system 104 comprising a computer 105 mounted on the cart 102 in accordance with the present invention is shown in FIG. 1. For convenience, the computer 105 is rotatably mounted on the top T of the cart 102 in any of a number of well known manners. The computer system 104 includes a conventional display 106 for displaying data and a conventional keyboard 108, a bar code reader 110 and a magnetic strip reader 111 for inputting data into a central processing unit 308, see FIG. 3. A computer which is suitable for use in the present invention is commercially available from AST Corporation, Irvine, Calif. under the tradename GRID Convertible SL25 computer.

The computer system 104 further includes a transmitter and receiver device 112 for transmitting and receiving data. Although the transmitter and receiver device 112 is shown external to the computer 105, as those skilled in the art will readily comprehend, the transmitter and receiver device 112 may be integral with the transmitter and receiver. The device 112 preferably transmits and receives data through spread spectrum radio frequency signals. Using spread spectrum techniques to transmit and receive data is well known in the art. In brief, the transmitter and receiver device 112 scans a defined frequency range to locate a frequency which is not being used. The device 112 then transmits data at this frequency. Conversely, the device 112 also continually scans the frequency range for incoming signals. A commercially available spread spectrum radio frequency transmitter and receiver is manufactured by American Telephone and Telegraph Corporation, Utrecht, Holland as WaveLan.

The cart 102 has a medication storage compartment 114 for storing medications to be dispersed during a patient round. A handle 115 facilitates opening and closing the medication storage compartment 114. The medication storage compartment 114 may include any number of conventional storage facilities, such as removable trays, drawers, slots, or the like. A lock 116 on an access door of the medication storage compartment 114 prohibits unwanted access to the medications stored therein.

A plurality of wheels 118 are mounted on the cart 102 which permit ready transport of the cart. 102 during patient rounds. To reduce damage resulting from the cart 102 striking walls and the like, rubber bumpers 120, 122 radially extend from the respective upper and lower perimeters of the cart 102. A waste compartment 124 is mounted on the cart 102 for disposing of medicine containers and other waste. Preferably, the waste compartment 124 is readily removable from the cart 102 such that accumulated waste may be easily transferred to a larger waste container.

Figure 1A:
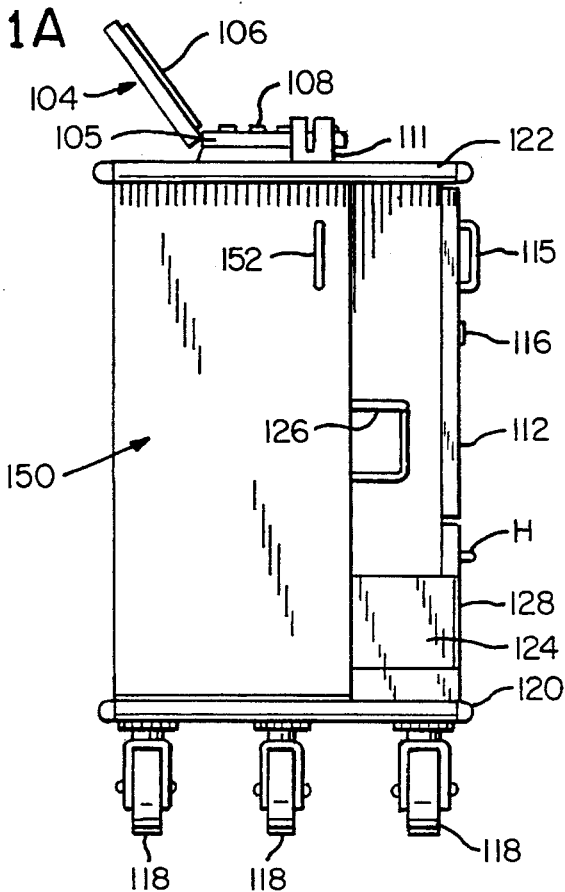
FIG. 1A is a side view of the mobile nursing unit shown in FIG. 1.
Figure 1B:
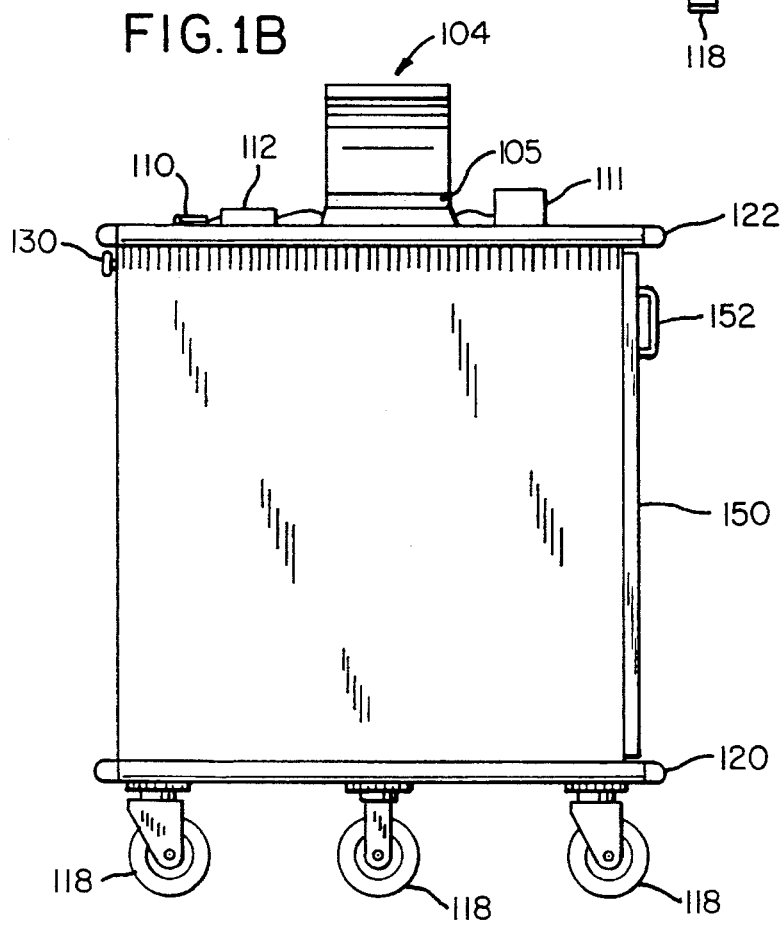
FIG. 1B is a rear view of the mobile nursing unit shown in FIG. 1.
Figure 4B:
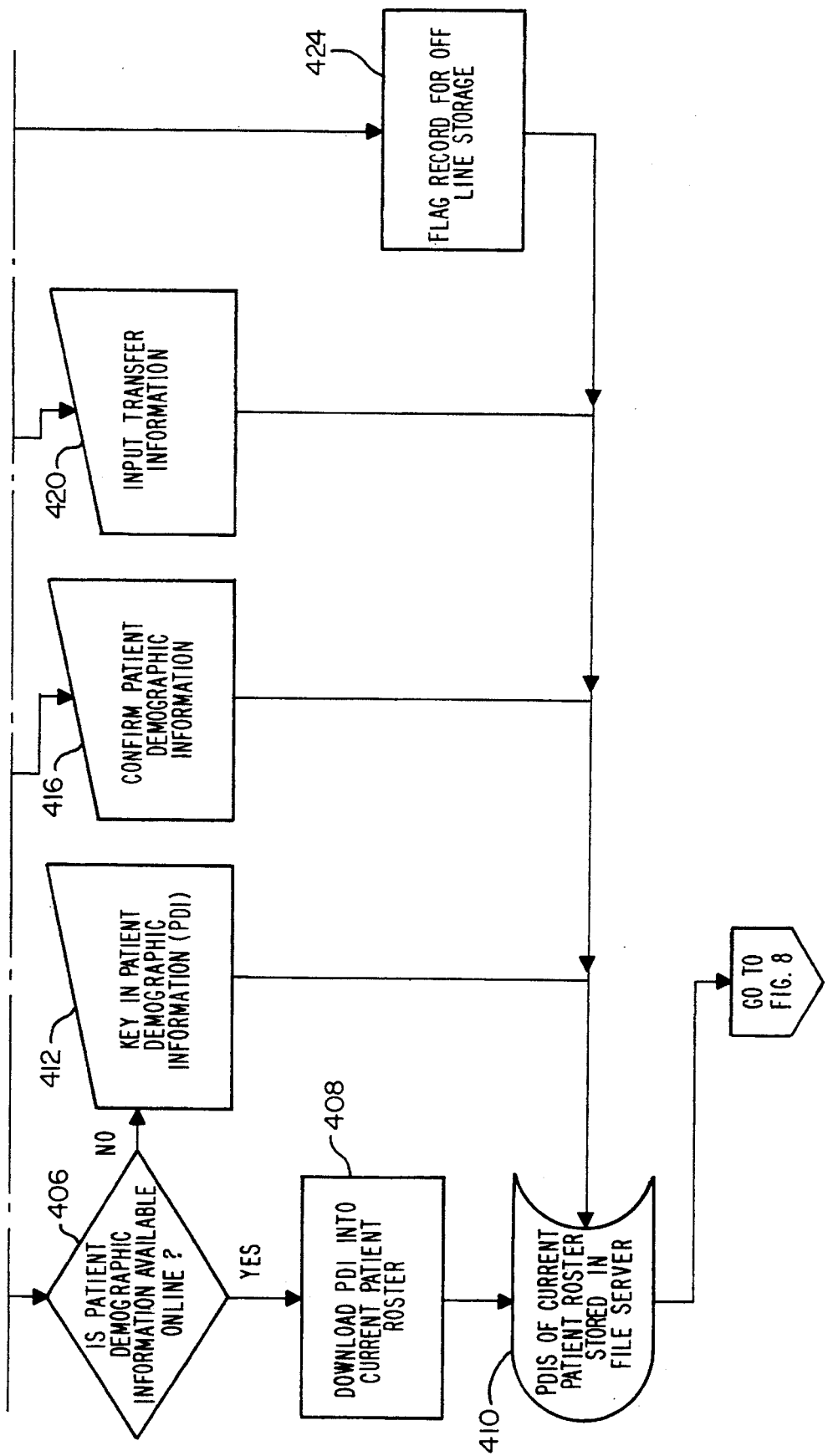
Figure 5A:
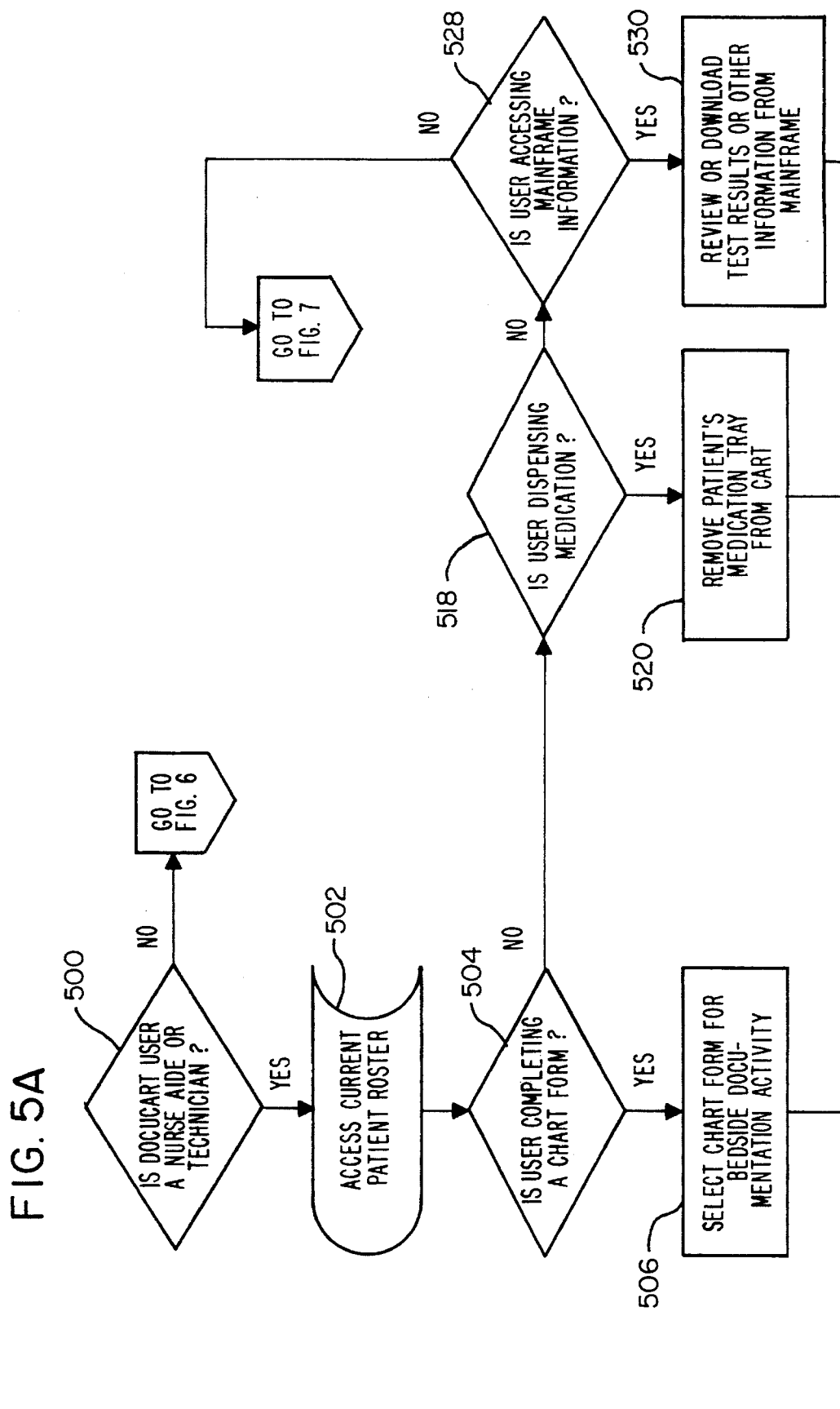
Figure 5B:
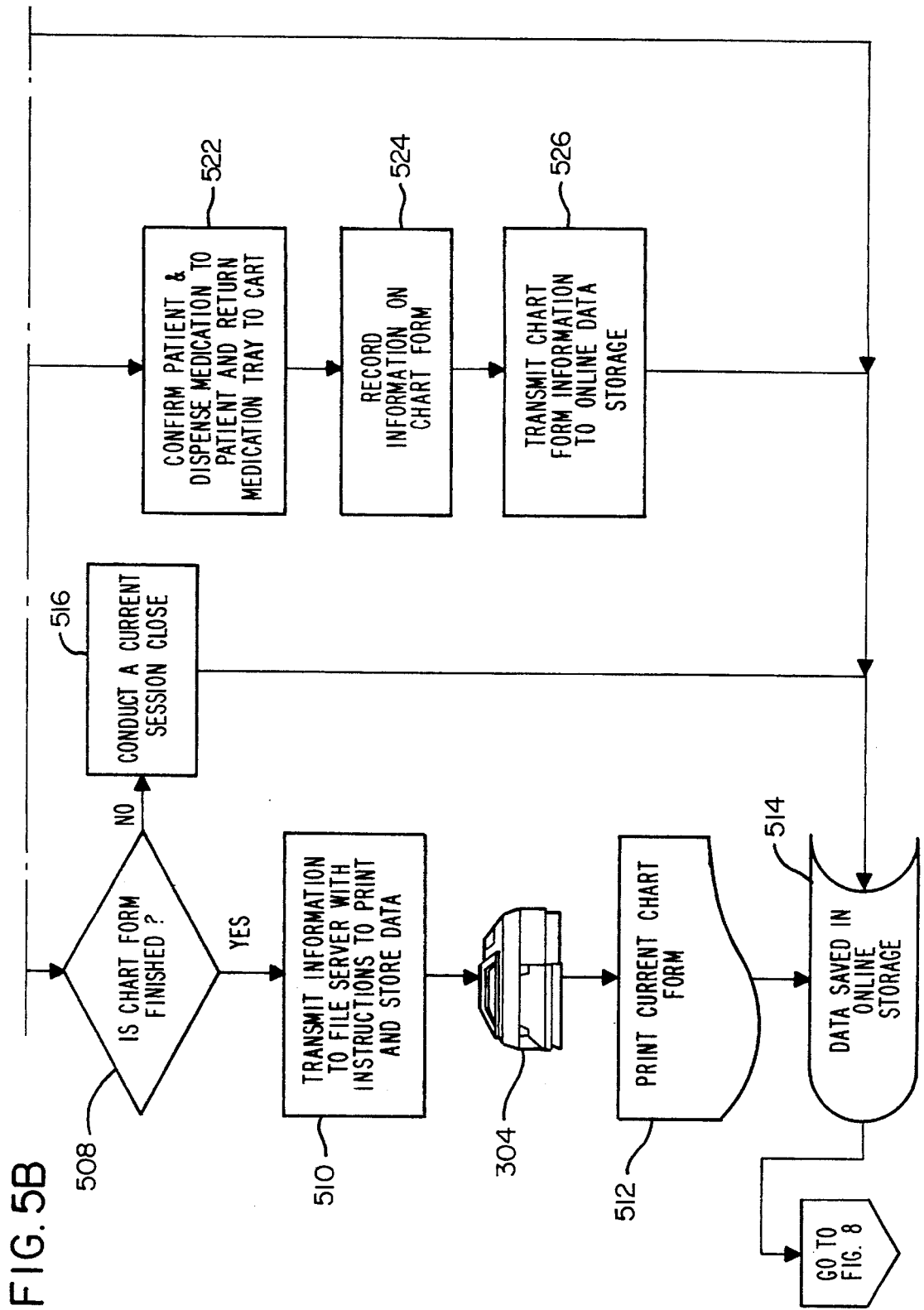

A wire guide 126 is mounted on the cart 102 for transporting medical diagnostic instruments, such as a conventional portable sphygmomanometer. The cart 102 also includes a supplies drawer 128 having a handle 130 for storing other medical supplies, such as bandages, IV tubes and needles. A pullout top 130 provides a retractable surface for writing and the like. As shown in FIG. 1A, a side compartment 150 having a handle 152 is provided for storing additional supplies.

A system 300 for providing and documenting patient care is shown in FIG. 3. Hereinafter, components which are common to the figures are identified by the same reference numerals. A remote computer system 302 including a printer 304 transits data to and receives data from the mobile computer system 104 mounted on the cart 102 via a radio frequency transmitter and receiver 306. The remote computer system 302 may be configured in any of a number of ways and may be located at any convenient location, such as at the nursing unit desk on the patient floor. Typically, a remote computer system will be located at the nursing unit desk for use by the unit secretary and a mainframe computer system will be centrally located in the facility.

It should be understood that the remote computer system 302 may also communicate with the mainframe computer system via spread spectrum radio frequency signals. The mobile computer system 104 transmits data to and receives data from the remote computer system 302 through the transmitter and receiver device 112. Preferably, the remote computer system 302 and the mobile computer system 104 transmit and receive data through radio frequency signals using conventional spread spectrum techniques.

The computer 105 includes a conventional central processing unit 308 for processing data in accordance with a computer program in a well known manner. A forms generator 310 responsive to the central processing unit 308 generates patient forms based on data received from the remote computer system 302. The forms generator 310 also modifies the charts based on data inputted by the nurse. The modified charts can then be transmitted to the remote computer system 302 for printing by the printer 304. This downloading and printing of updated charts may be accomplished substantially simultaneously with the nurse's rounds. After the nurse has completed a round, the updated patient charts are collected and placed in the permanent patient files.

A chargeable item archive 312 stores the type and amount of supplies expanded on each patient. This information is then used to calculate a patient's bill. The central processing unit 308 retrieves patient information from a patient archive 314. The patient archive 314 stores patient information download from the remote computer system 302 or other electronic storage device and updates the patient information in response to the central processing unit 308. As will be readily understood by those skilled in the art, the forms generator 310, the chargeable item archive 312 and the patient archive 314 may be embodied in a single processor, such as central processing unit 308, or in a variety of memory devices.

The operation of the system 300 will now be described with reference to the flow charts shown in FIGS. 2 and 4 through 8. A flow chart illustrating an exemplary operating procedure which is followed by a nurse using the present invention is shown in FIG. 2. Upon beginning a shift, the nurse is assigned a number of patients and a designated mobile nursing unit at step 200. The nurse, at step 202, then completes workplans and stocks the mobile nursing unit with chargeable and nonchargeable supplies and medications for the patients. The nurse then logs onto the system 300.

The nurse begins the patient rounds, shown at step 204. At each patient's bedside, the nurse may retrieve information relating to the patient's care from the remote computer system 302 through the mobile computer system 104, see step 206. The nurse also dispenses medications and chargeable supplies and updates the patient's records through the mobile computer system 104. As each chart of the patient's records is completed, the chart is transmitted via spread spectrum radio frequency signals to the remote computer system 302 which may be located at the nursing station on the floor at step 208. The updated charts may then be printed by the printer 304. The updated printed charts are then inserted into the patient's permanent records. At the end of the shift, the nurse, at step 210, returns unused chargeable supplies to a supply room. The nurse then logs off the system 300 and stores the mobile nursing unit 100 in a designated area.

The operational sequence 400 for accessing or completing an electronic patient chart is illustrated in FIGS. 4 through 8. The operational sequence 400 may be implemented by a computer program stored in the central processing unit 308 of the mobile nursing unit 100. Initially, it is determined whether a unit secretary is accessing the patient chart at step 402. If the operator is a unit secretary, it is then determined if the patient is being admitted, at step 404. If the patient is being admitted, it is determined whether the patient already has demographic information stored in the remote computer 302, at step 406. At step 408, if the patient information is stored in the remote computer system 302, the information is downloaded into the mobile computer system 104 and, at step 410, the patent information is stored in the patient archive 314. If, at step 406, the patient demographic information was not already recorded, the patient demographic information is inputted into the system 104 at step 412 and the information is downloaded at step 410.

If the patient is not being admitted at step 404, it is determined whether the patient is being transferred from another floor, or department, at step 414. If yes, then the patient demographic information is checked and confirmed at step 416 and the information is downloaded at step 410. If the patient is not being transferred from another unit, it is determined whether the patient is being transferred from another location at step 418. If yes, the transfer information is inputted into the system at step 420. If not, the patient is being discharged at step 422 and the patient's record is flagged for storage at an off line location at step 424. After being downloaded at step 410, the data is checked to determine if it is flagged for off line storage, see FIG. 8 at step 800. If the data is flagged, the data is moved to off line storage, at step 802, and stored at step 804. The off line storage may be any of a number of electronic storage devices, such as CD-ROM, computer tape, and the like.

If the user is not a unit secretary, at step 402, it is determined whether the user is a nurse's aid or a technician at step 500. If the user is a nurse's aid or a technician, the user is given access to the current patient roster at step 502. It is then determined whether the operator is completing a chart form at step 504. If so, the appropriate chart form is selected at step 506. If the chart form is finished at step 508, the information is transmitted to the remote computer system 302 with instructions to print, via the printer 304, and store the information at step 510. The updated information is then printed at step 512 and the data is saved, at step 514, in the remote computer system 302.

In the event that the chart form is not finished at step 508, such as when additional information is needed, the current session is closed at step 516 and the information stored in the remote computer system at step 514. Consequently, the operator may continue on a round and add information later.

If the operator is not completing a chart form at step 504, it is determined whether the user is dispensing medications at step 518. If so, the user removes the patient's medication tray from the cart 102 at step 520. The user then confirms the patient identity and the medication and dispenses the medication to the patient 522. The dispensed medication is then recorded on the appropriate chart form at step 524 and the updated chart form information is transmitted to the remote computer system 302 for storage or printing at step 526. If the user is not dispensing medication, it is determined whether the user is accessing mainframe information at step 528. If so, the mainframe information is reviewed or downloaded from the mainframe at step 530 and saved by the remote computer system 302. Each time the remote computer saves information, the information may be saved at an off line location, such as at a mainframe computer and the like, at step 800.

If the user is not accessing mainframe information at step 528, it is determined whether the user is scanning a chargeable item at step 700. If not, the program returns to FIG. 4. If so, the patient's identity is verified at step 702 and the item is scanned at the patient's bedside at step 704. The item charge is then transmitted via radio frequency signals to the remote computer 302, or the mainframe computer. The chargeable item information is typically stored in the mainframe computer such that all patient bills may be generated at a common area. Thereafter, the charges are organized by the mainframe computer to generate the final patient bill at step 708 and the program returns to FIG. 4 at step 710.

If the user is not a nurse's aid or technician at step 500, the user is a physician, at step 600. The physician has access to data saved at the remote computer system 302 at step 602. Preferably, the physician carries a hand held portable computer system during rounds. The hand held portable computer system is a portable version of the computer system 104 and is capable of transmitting and receiving data from the remote computer system 302 and the mainframe computer.

It is next determined whether the physician is documenting an activity at step 604. If so, the physician documents the activity via the portable computer system 302 at step 606 and the data is transmitted for storage to the remote computer system at step 608. If the physician is not documenting an activity at step 604, it is determined whether the physician is referencing information which has been stored at step 610. If so, the information is provided and the session is closed at step 612.

After storage of information in the remote computer system 302, the data is checked for offline storage, see FIG. 8 at step 800. As noted above, the offline storage medium may be computer tapes, CD-ROMs or the like. If the data is to be stored offline, it is transmitted to the offline storage at step 802. The data may be transmitted through radio frequency signals or other means. The data is then stored on the appropriate medium.

Having thus described the invention in detail by way of reference to preferred embodiments thereof, it will be apparent that other modifications and variations are possible without departing from the scope of the invention defined in the appended claims.

What is claimed is:

1. A mobile nursing unit comprising::
    a cart for storing and transporting medicines and medical supplies, said cart including a plurality of wheels mounted on said cart for permitting movement of said cart; and
    a computer system mounted on said cart including
        a central processing unit,
        a transmitter and receiver device responsive to said central processing unit for transmitting and receiving data, said transmitter and receiver system being capable of transmitting and receiving data through radio frequency signals,
        an input device for inputting data into said computer system, and
        a display responsive to said central processing unit for displaying data.

2. The mobile nursing unit as set forth in claim 1 wherein said cart comprises a waste compartment mounted on said cart for disposing of waste.

3. The mobile nursing unit as set forth in claim 1 wherein said cart comprises a medication storage compartment for storing medications.

4. The mobile nursing unit as set forth in claim 3 wherein said cart comprises a lock for locking medications in said medication storage compartment.

5. The mobile nursing unit as set forth in claim 1 wherein said input device comprises a bar code reader.

6. The mobile nursing unit as sell forth in claim 1 wherein said input device comprises a keyboard.

7. The mobile nursing unit as set forth in claim 1 wherein said input device comprises a magnetic strip reader.

8. The mobile nursing unit as set forth in claim 1 wherein said computer system comprises a forms generator responsive to said central processing unit for generating a plurality of forms for charting patient care.

9. The mobile nursing unit as set forth in claim 1 wherein said transmitter and receiver device comprises a spread spectrum transmitter and receiver for transmitting and receiving data.

10. The mobile nursing unit as set forth in claim 1 wherein said computer system comprises a patient archive responsive to said central processing unit for storing information concerning patients.

11. The mobile nursing unit as set forth in claim 1 wherein said central processing unit comprises a chargeable item archive for identifying and storing medical supplies used on a patient.

12. A mobile nursing unit comprising:
    a cart including,
        a medication storage compartment for storing medications, said medication storage compartment including a lock for locking said medication storage compartment,
        a medical supplies compartment for storing medical supplies,
        a waste compartment for storing waste, and
        a plurality of wheels for permitting movement of said cart; and
    a computer system mounted on said cart including,
        a central processing unit,
        a transmitter and receiver system responsive to said central processing unit for transmitting and receiving data, said transmitter and receiver system capable of transmitting and receiving data through radio frequency signals and capable of operating over a spread spectrum,
        a display responsive to said central processing unit for displaying data, and
        an input device for inputting data into said computer system.

13. The mobile nursing unit as set forth in claim 12 wherein said computer system comprises a patient archive responsive to said central processing unit for storing information concerning patients.

14. The mobile nursing unit as set forth in claim 13 wherein said computer system comprises a chargeable item archive responsive to said central processing unit for identifying and recording the type and amount of medical supplies used for a patient.

15. The mobile nursing unit as set forth in claim 12 wherein said computer system comprises a forms generator responsive to said central processing unit for generating a plurality of forms for charting patient care.

16. A system for providing patient care and for documenting patient care comprising:
- a remote computer system for transmitting data, for storing data and for receiving data, said remote computer system including a remote transmitter and receiver device for transmitting and receiving data through radio frequency signals;
- a printer responsive to said remote computer system for printing documents indicative of patient care; and
- a plurality of mobile nursing units, each of which comprise:
  - a cart for storing medications and medical supplies, said cart including a plurality of wheels for permitting movement of said cart, and
  - a computer system mounted on said cart, said computer system comprising,
    - a central processing unit,
    - a unit transmitter and receiver device for transmitting data to said remote transmitter and receiver device and for receiving data from said remote transmitter and receiver device, said unit transmitter and receiver device being capable of transmitting and receiving data through radio frequency signals,
    - an input device for inputting data into said computer system, and
    - a display responsive to said central processing unit for displaying data.

17. The system as set forth in claim 16 wherein said cart comprises:
- a medication storage compartment for storing medications; and
- a lock for locking medications in said medication storage compartment.

18. The system as set forth in claim 16 wherein said computer system comprises a forms generator responsive to said central processing unit for generating a plurality of forms for charting patient care.

19. The system as set forth in claim 16 wherein said unit transmitter and receiver device transmits and receives said radio frequency signals in spread spectrum format and wherein said remote transmitter and receiver device transmits and receives said radio frequency signals in spread spectrum format.

20. The system as set forth in claim 16 wherein said input device comprises a bar code reader.

* * * * *